(12) United States Patent
Voelkel

(10) Patent No.: US 7,937,155 B1
(45) Date of Patent: *May 3, 2011

(54) ENVELOPE-BASED AMPLITUDE MAPPING FOR COCHLEAR IMPLANT STIMULUS

(75) Inventor: Andrew W. Voelkel, Venice, CA (US)

(73) Assignee: Advanced Bionics, LLC, Valencia, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 12/430,894

(22) Filed: Apr. 28, 2009

Related U.S. Application Data

(60) Division of application No. 11/346,067, filed on Feb. 2, 2006, now Pat. No. 7,542,806, which is a continuation of application No. 10/684,863, filed on Oct. 14, 2003, now Pat. No. 6,996,438, which is a division of application No. 09/866,096, filed on May 25, 2001, now Pat. No. 6,728,578.

(60) Provisional application No. 60/208,627, filed on Jun. 1, 2000.

(51) Int. Cl.
*A61N 1/02* (2006.01)
(52) U.S. Cl. ........................................................ 607/56
(58) Field of Classification Search ............... 607/55–57, 607/136, 137; 300/25; 623/10
See application file for complete search history.

(56) References Cited

U.S. PATENT DOCUMENTS

| | | | | |
|---|---|---|---|---|
| 4,284,856 A * | 8/1981 | Hochmair et al. | ................. | 607/9 |
| 4,611,598 A * | 9/1986 | Hortmann et al. | ............... | 607/57 |
| 5,069,210 A * | 12/1991 | Jeutter et al. | ..................... | 607/57 |
| 5,271,397 A * | 12/1993 | Seligman et al. | ............. | 607/137 |
| 5,323,467 A * | 6/1994 | Hermes | .......................... | 381/94.3 |
| 5,749,912 A * | 5/1998 | Zhang et al. | ..................... | 607/57 |
| 5,824,022 A * | 10/1998 | Zilberman et al. | .............. | 607/57 |
| 5,848,171 A * | 12/1998 | Stockham et al. | ............. | 381/321 |
| 5,983,139 A * | 11/1999 | Zierhofer | ......................... | 607/56 |
| 6,157,861 A * | 12/2000 | Faltys et al. | ..................... | 607/57 |
| 6,728,578 B1 * | 4/2004 | Voelkel | ........................... | 607/56 |

\* cited by examiner

*Primary Examiner* — Carl H Layno
*Assistant Examiner* — Gary A Porter, Jr.
(74) *Attorney, Agent, or Firm* — Bryant R. Gold

(57) ABSTRACT

An envelope based amplitude mapping achieves the signal compression required to provide a natural sound level without the high processor loading or waveform alteration. In one embodiment, the output of a family of parallel bandpass filters is processed by an envelope detector, followed by decimation. The resulting reduced data rate envelope is log mapped to produce a scaling factor for the original high data rate bandpass filter output sequence. The resulting scaled signal determines the current level for stimulation of the cochlea for each frequency band, which stimulation achieves a log mapping of the sound amplitude effect similar to natural hearing, while reducing processor load, and preserving waveform shape.

12 Claims, 4 Drawing Sheets

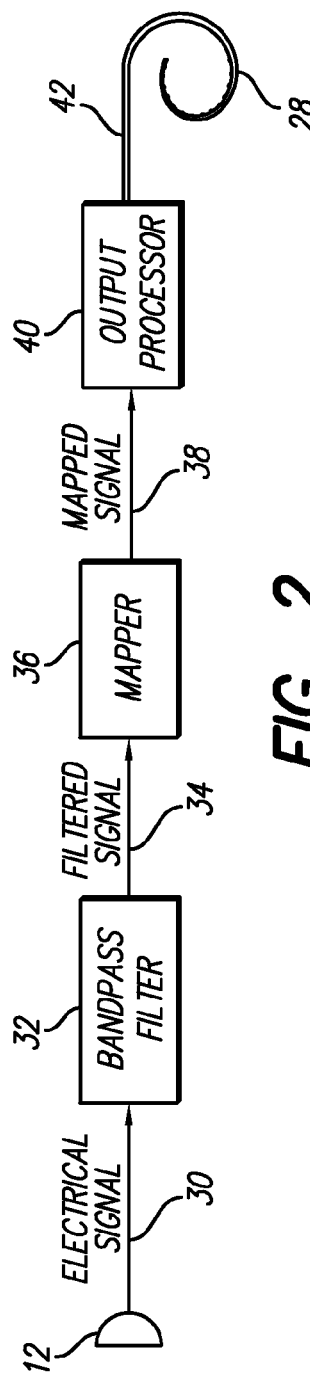
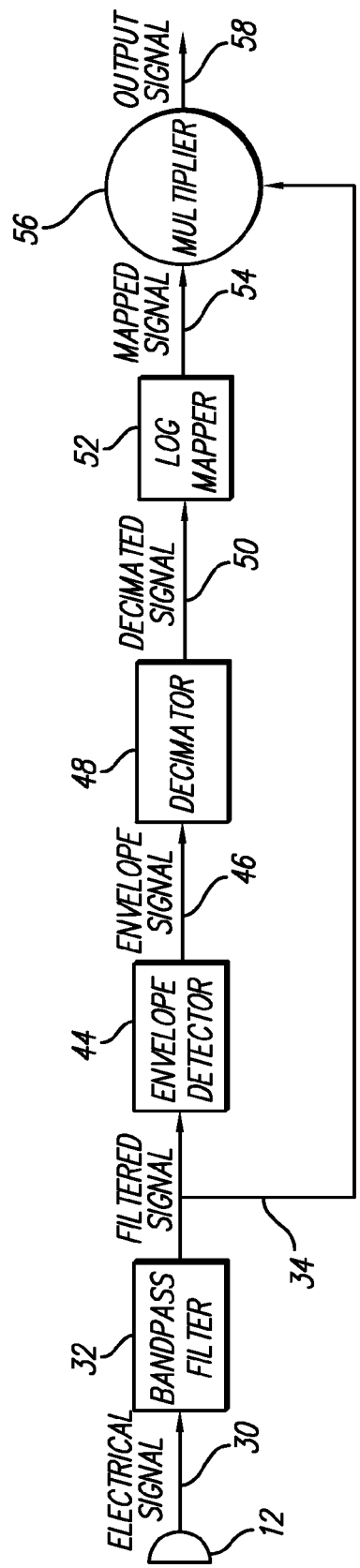

ENVELOPE-BASED AMPLITUDE MAPPING FOR COCHLEAR IMPLANT STIMULUS

The present application is a Divisional of U.S. application Ser. No. 11/346,067, filed Feb. 2, 2006, now issued as U.S. Pat. No. 7,542,806; which is a Continuation of U.S. application Ser. No. 10/684,863, filed Oct. 14, 2003, now issued as U.S. Pat. No. 6,996,438; which is a Divisional of U.S. application Ser. No. 09/866,096, filed May 25, 2001, now issued as U.S. Pat. No. 6,728,578; which claims the benefit of U.S. Provisional Application Ser. No. 60/208,627, filed Jun. 1, 2000, which applications and patent are incorporated herein by reference.

BACKGROUND OF THE INVENTION

The present invention relates to cochlear prosthesis used to electrically stimulate the auditory nerve, and more particularly to a process for mapping a signal level into a stimulation current level.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, numerous implantable cochlear stimulation systems—or cochlear prosthesis—have been developed which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominators in most of these cochlear prosthesis systems have been the implantation, into the cochlea, of electrodes, and a suitable external source of an electrical signal for the electrodes.

A cochlear prosthesis operates by direct electrical stimulation of the auditory nerve cells, bypassing the defective cochlear hair cells that normally transduce acoustic energy into electrical activity in such nerve cells. In order to effectively stimulate the nerve cells, the electronic circuitry and the electrode array of the cochlear prosthesis perform the function of separating the acoustic signal into a number of parallel channels of information, each representing the intensity of a narrow band of frequencies within the acoustic spectrum. Ideally, the electrode array would convey each channel of information selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex, and ideally the entire length of the cochlea would be stimulated to provide a full frequency range of hearing. In practice, this ideal is not achieved, because of the anatomy of the cochlea which decreases in diameter from the base to the apex, and exhibits variations between patients. Because of these difficulties, known electrodes can only be promoted to the second turn of the cochlea at best.

The signal provided to the electrode array is generated by a signal processing component of the Implantable Cochlear Stimulation (ICS) system. In known ICS systems, the acoustic signal is first processed by a family of parallel bandpass filters. Next the output of each bandpass filter is independently amplitude mapped into a simulation level using a mapping consistent with normal perception. In known systems, the mapping is a compressive mapping that is based on the log of the magnitude of each independent sample of the outputs of the band pass filters. The log is taken of the magnitude of each sample, then multiplied by a first scalar and added to a second scalar, and the sign of each sample is then applied to the compressed value. Disadvantageously, the log function can result in a DC component in the resulting signal, distorts sinusoidal inputs, and is computationally intensive.

The DC component arises from the asymmetry of the input waveform. The signal is processed before the amplitude mapping to remove DC bias, and as a result the total area under the waveform, at the output of the bandpass filters, sums to zero. But, the compressive nature of the log function reduces narrow high peaks much more than wide low peaks, and thereby creates a DC bias. A wideband speech signal is very asymmetric by nature, so the likelihood of generating such a DC bias is high. The presence of the DC bias poses a potential for tissue damage after long term use, and may cause the charge in a capacitor typically, used for energy storage in the implantable stimulation circuit, to grow large resulting in undesirable nonlinear behavior.

The shape of a waveform processed by the amplitude mapping may be distorted by the compression. For example, samples from the peak of a sinusoidal waveform are compressed more than samples between the peaks, and as a result the sinusoid becomes more like a square wave with rounded corners than like a sinusoid. When patients are tested for psychophysical thresholds, sine waves are used as the stimulating signals for each electrode. The frequency of each sine wave is selected as the center frequency of the band pass filter that processes the signal for the corresponding electrode in normal system operation. When the threshold levels determined during psychophysical testing are later applied to a compressed sinusoid, which compressed sinusoid has the same peak stimulating current as the original sinusoid that the thresholds are based on, the perceived loudness may not be the same as with the original sinusoid. Although the peak stimulation currents of the original sinusoid and the compressed sinusoid are the same, the amplitude mapping brings up the "shoulders" on the compressed sinusoid, making it more like a square wave with rounded corners. As a result of "raising the shoulders" of the sinusoid, charge per phase raises, which results in the perceived loudness increasing. This increase in perceived loudness may be significant for patients with a narrow dynamic hearing range.

The processing required to compute the log of each sample, in each frequency band, at a high data rate, is a computationally demanding process that expends significant power in the signal processor. The development of Behind-The-Ear (BTE) speech processor, and fully implantable cochlear stimulators, requires that power consumption be reduced to a minimum. A BTE ICS system is described in U.S. Pat. No. 5,824,022 issued Oct. 20, 1998 for 'Cochlear stimulation system employing behind-the-ear speech processor with remote control.' Behind-the-ear speech processors offer several advantages, but their small size limits the size of the battery they may carry (which in turn limits the capacity of the battery.) The small battery size results in a requirement for very low power consumption. Processing, such as that required by known amplitude mapping methods, work against the need to reduce power dissipation. The '022 patent is herein incorporated by reference.

An improvement to the current compressive processing is needed to both improve performance, and to reduce the power consumption required for signal processing.

SUMMARY OF THE INVENTION

The present invention addresses the above and other needs by replacing the known sample by sample amplitude mapping process in Implantable Cochlear Stimulation (ICS) systems with an envelope based amplitude mapping process. The envelope based amplitude mapping processes operate in parallel on the filtered signals output from parallel bandpass filters. The filtered signal is first processed by an envelope detector. The result of envelope detection is decimated, and the resulting decimated envelope is transformed using a compressive function, which compressive function is the product of a log mapping of the decimated envelope and a reciprocal of the decimated envelope. The transformed signal is then used to scale the original filtered signal to obtain the stimulation current level for the implanted cochlear electrode array.

In accordance with one aspect of the invention, there is provided an envelope detector. In a preferred embodiment, the envelope detector is a full wave rectifier followed by a lowpass filter. The lowpass filter cutoff frequency is chosen so as to block the high frequency fluctuations of individual samples of the audio component of the rectified signal, but pass the local averaged value of the signal. The preferred cutoff frequency is around 100 Hz, which cutoff determines the lowpass filter design.

It is a further feature of the invention to decimate the signal envelope to reduce the number of samples processed by the log mapping. The log function is computationally intensive, and places a heavy load on the speech processor. Such high processing loads result in increased power consumption. By reducing the number of samples that the log function operates on, the overall loading of the speech processor is similarly reduced, thus reducing power consumption. In a preferred embodiment of the invention the decimation factor is 1:16. Such power savings are very important to both Behind-The-Ear ICS systems, and to fully implantable ICS systems.

It is an additional feature of the present invention to provide a scaling of the bandpass filter outputs based on a transform which is a function of the log of the decimated envelope. This approach advantageously retains the shape of the waveform because the scaling is based on a measure of the smoothed signal level in the locality of the sample to be scaled, instead of being a function of a single sample, as in known speech processors.

BRIEF DESCRIPTION OF THE DRAWINGS

The above and other aspects, features and advantages of the present invention will be more apparent from the following more particular description thereof, presented in conjunction with the following drawings wherein:

FIG. 2 depicts a functional flow for a prior-art amplitude mapping;

FIG. 3 depicts a functional flow for envelope based amplitude mapping.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
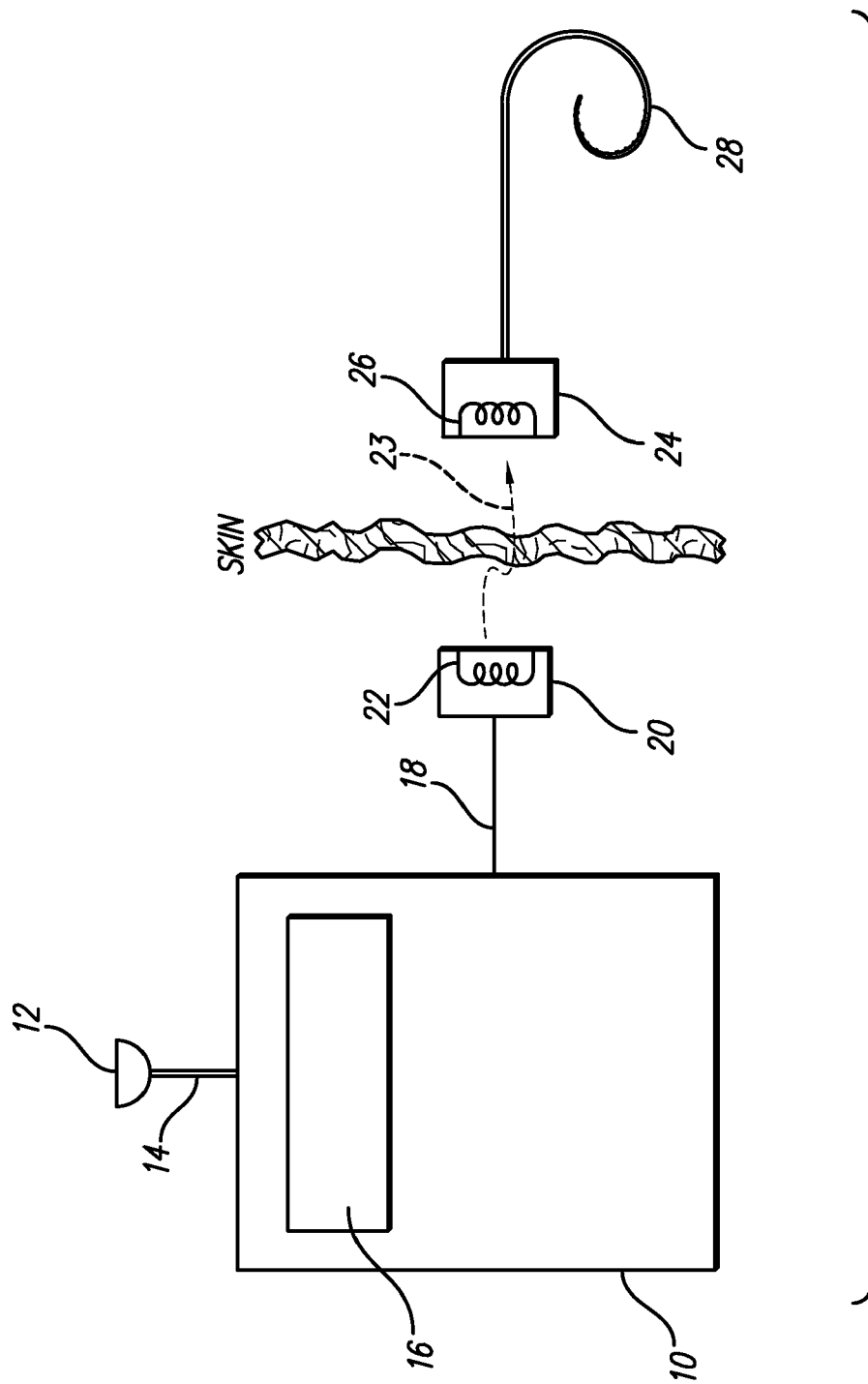
FIG. 1 shows the major elements of a known Implantable Cochlear Stimulation (ICS) system.

A functional diagram of a typical Implantable Cochlear Stimulation (ICS) system is shown in FIG. 1. The ICS includes a speech processor 10 that could be a wearable speech processor, or a Behind-The-Ear (BTE) speech processor. A microphone 12 may be connected to the speech processor 10 by a first wire 14, or may be attached to the speech processor 10 as in the case of a BTE speech processor. The microphone 12 converts acoustic energy into an electrical signal for subsequent processing. The speech processor 10 contains a signal processor 16 that processes the electrical signal from the microphone 12. The output signal of the signal processor 16 is carried by a second wire 18 to a headpiece 20 carried on the patient's head. A first coil 22 transmits the control signal 23 from the headpiece 20 to the implantable electronics 24, which implantable electronics 24 includes a second coil 26 for receiving the control signal. The implantable electronics 24 processes the control signal 23 to generate stimulation current for the electrode array 28, which electrode array 28 is implanted in the patient's cochlea.

The architecture of an ICS system may vary. The ICS may include a wearable speech processor that is worn on the users belt and is connected to a microphone and headpiece by wiring, or a Behind-The-Ear (BTE) speech processor resembling a typical hearing aid, that is worn behind the patient's ear and retained by an earhook. Another example is a fully implantable ICS in which a speech processor 10 is integrated into the implantable electronics 26. Those skilled in the are will recognize that all of these variations require a microphone (or more generally a transducer), and a signal processor, to provide a stimulation level. All of these variations benefit from the present invention as described below.

The human ear adjusts sound intensity with a logarithmic like scaling. Thus, if a sound is 10 times stronger, it may only be perceived to be twice as loud. ICS systems must perform a similar scaling, or mapping, if the patient is to perceive sounds with a natural intensity. Additionally, such logarithmic scaling has the advantage of providing intelligible hearing for low level sounds, without overwhelming the patient when loud sounds are encountered.

A functional flow for a single channel of prior-art amplitude mapping is shown in FIG. 2. In known systems, there may be from 4 to 30 such parallel channels operating in different frequency bands. The microphone 12 provides an electrical signals to a bandpass filters 32. The bandpass filter 32 process the electrical signal 30 to generate a filtered signal 34. The filtered signal 34 is then processed by a mapper 36 which outputs the mapped signal 38. The mapper 36 maps the electrical signal 30 level measured by the microphone 12 into an electrical stimulation level to be provided to the electrode array 28. In a preferred embodiment the mapper 36 is a log mapper, reflecting normal human hearing. Those skilled in the are will recognize that other mapping may produce similar results and those other mappings are within the scope of the present invention. The mapped signal 38 is processed by output processing 40 which outputs the stimulation signal 42 which is provided to the electrode array 28. The log mapper 36 operates on every signal processed by the amplitude mapping.

A first embodiment of the present invention, depicted by one channel of an envelope based amplitude mapping applied to Simultaneous Analog Stimulation (SAS), is shown in FIG. 3. In practice, there are from 4 to 30 such parallel channels operating in different frequency bands. The processing up to and including the bandpass filter 32 is unchanged from known systems. The sample rate for the filtered signal 34 is between 10 KHz and 25 KHz and is preferably 13 KHz or 17 KHz. Identical filtered signals 34 produced by the bandpass filter 32 are carried on two paths. The top paths in FIG. 3 represents the heart of the envelope based amplitude mapping. An envelope detector 44 computes an envelop signal 46 from the filtered signal 34. In a preferred embodiment the envelope detector 44 is a full wave rectifier followed by a lowpass filter with a cutoff of 100 Hz. The particular envelope detector 44 that is best for a specific ICS system depends on the details of processing that precedes the envelope detector 44. Various other implementations of envelope detectors will be apparent to those skilled in the art, and these variations are intended to fall within the scope of the present invention.

The next step in the processing shown in FIG. 3 is a decimator 48. The decimator 48 creates a decimated signal 50 by reducing the sample rate by only passing every $M^{th}$ value of the envelope signal 46. The sample rate of the decimated signal 50 may be between 50 Hz and 1000 Hz and is 800 Hz in a preferred embodiment. The decimated sample rate in other embodiments of the invention may vary based on other parameters of ICS the present invention is exercised in, and on the preferences of the patient. While the envelope detector and decimator are shown as separate processing steps, in a preferred implementation, the lowpass filter and decimator are combined into a single Finite Impulse Response (FIR) filter.

Continuing on in FIG. 3, a log mapper 52 computes a mapped signal 54 from the decimated signal 50 by taking a compressive transformation of the decimated signal 50. The preferred transformation is of the form $F'(x)=F(x)/x$, where $F(x)=C1*\log(x)+C2$. The division by x is required due to the multiplying step described below. C1 and C2 are based on psycho-acoustical phenomena and are patient dependent. Specifically, during a fitting process, measurements are made for each patient, and C1 and C2 are determined for the individual patient based on those measurements.

The mapped signal 54 may be viewed as a scaling factor related to the average level of the filtered signal 34 in the locality of the sample the scaling is applied to. A multiplier 56, multiplies the mapped signal 54 times the original filtered signal 34, to generate an envelope based amplitude mapping output signal 58. The mapped signal 54 sample rate (hereafter the second sample rate) is lower than the filtered signal 34 sample rate (hereafter the first sample rate.) If the first sample rate is not substantially higher than the second sample rate, for example, the first sample rate is less than sixteen times the second sample rate, the mapped signal 54 may be used directly by the multiplier 56. If the first sample rate is substantially higher than the second sample rate, for example, the first sample rate is more than sixteen times the second sample rate, the mapped signal 54 may be linearly interpolated to the first sample rate.

Figure 4:
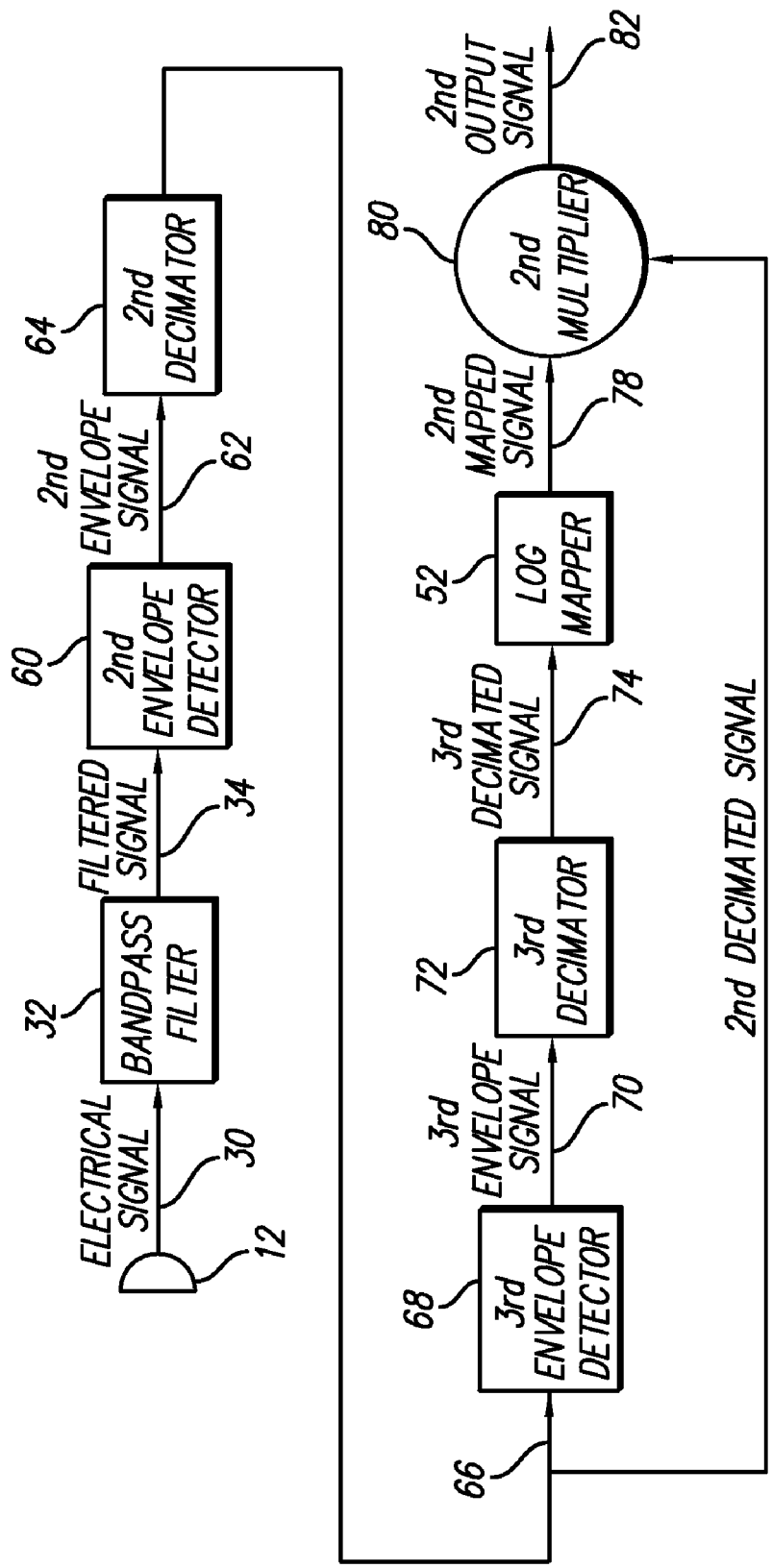
FIG. 4 depicts a flow chart for a CIS amplitude mapping application of the invention.

The envelope based amplitude mapping described above for SAS amplitude mapping may also be applied to Continuous Interleaved Sampler (CIS) amplitude mapping. A flow chart for a CIS amplitude mapping incorporating the present invention is shown in FIG. 4. The microphone 12 and bandpass filter 32 are the same as in FIGS. 2 and 3. The filtered signal 34 is processed by a second envelope detector 60 to produce a second envelope signal 62, and the envelope signal 62 is processed by a second decimator 64, to generate a second decimated signal 66. A preferred envelope detector 60 comprises a full wave rectifier and a low pass filter. The lowpass filter has a cut off frequency of about 800 Hz to 2000 Hz, preferably 800 Hz. While the envelope detector and decimator are shown as separate processing steps, in a preferred implementation, the lowpass filter and decimator are combined into a single Finite Impulse Response (FIR) filter.

Continuing with FIG. 4, the decimated signal 66 is processed by a third envelope detector 68 to obtain a third envelope signal 70, and the envelope signal 70 is processed by a third decimator 72 to obtain a third decimated signal 74. A preferred envelope detector 68 comprises a full wave rectifier and a low pass filter. The lowpass filter has a cut off frequency of about 40 Hz to 100 Hz, preferably 40 Hz. While the envelope detector and decimator are shown as separate processing steps, in a preferred implementation, the lowpass filter and decimator are combined into a single Finite Impulse Response (FIR) filter.

The decimated signal 74 is processed by the log mapper 52 to generate a second mapped signal 78. The mapped signal 78 and the decimated signal 66 are provided to the multiplier 80, resulting in the second output signal 82, which output signal 82 is provided to a pulse generator. One output signal 82 is provided for each pulse in CIS processing. The decimated signal 66 is at a higher data rate than the mapped signal 78. In a preferred embodiment, the mapped signal 78 is interpolated to the data rate of the decimated signal 66 in the multiplier 80.

Figure 5:
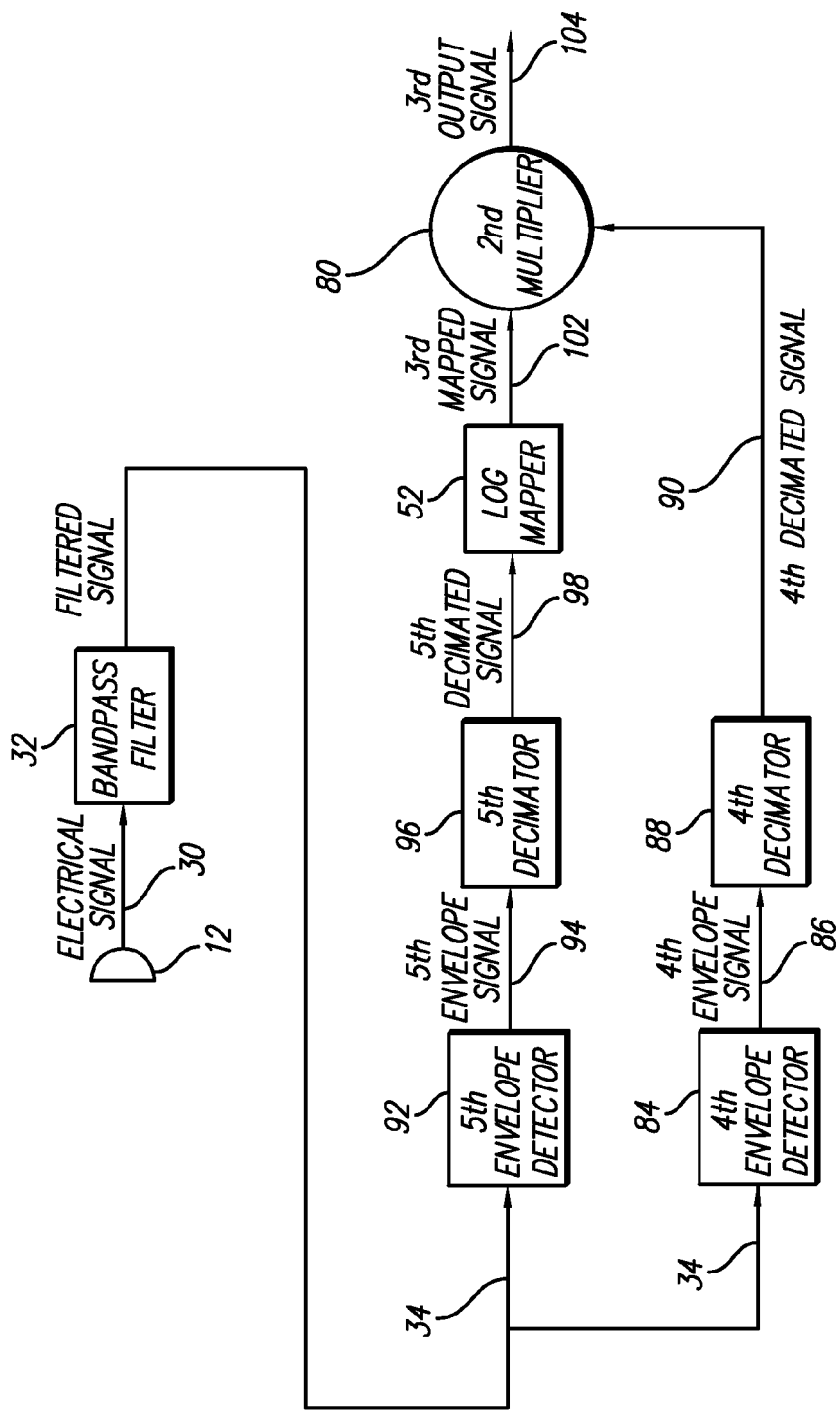
FIG. 5 depicts one embodiment of a flow chart for a CIS amplitude mapping application.

A third embodiment comprising a second application of the present invention to CIS amplitude mapping is shown in FIG. 5. The microphone 12 and bandpass filter 32 are the same as in FIGS. 2, 3, and 4. The filtered signal 34 is processed by two parallel paths in the second CIS embodiment. A fourth envelope detector 84 to produce a fourth envelope signal 86, and the envelope signal 86 is processed by a fourth decimator 88, to generate a fourth decimated signal 90. A preferred envelope detector 84 comprises a half wave rectifier and a low pass filter. The lowpass filter has a cut off frequency of about 800 Hz to 2000 Hz, preferably 800 Hz. While the envelope detector and decimator are shown as separate processing steps, in a preferred implementation, the lowpass filter and decimator are combined into a single Finite Impulse Response (FIR) filter.

Continuing with FIG. 5, the filtered signal 34 is processed by a fifth envelope detector 92 to obtain a fifth envelope signal 94, and the envelope signal 94 is processed by a fifth decimator 96 to obtain a fifth decimated signal 98. A preferred envelope detector 92 comprises a full wave rectifier and a low pass filter. The lowpass filter has a cut off frequency of about 40 Hz to 100 Hz, preferably 40 Hz. While the envelope detector and decimator are shown as separate processing steps, in a preferred implementation, the lowpass filter and decimator are combined into a single Finite Impulse Response (FIR) filter.

The decimated signal 98 is processed by the log mapper 52 to generate a third mapped signal 102. The mapped signal 102 and the decimated signal 90 are provided to the multiplier 80, resulting in a third output signal 104, which output signal 104 is provided to a pulse generator. One output signal 104 is provided for each pulse in CIS processing. The decimated signal 90 is at a higher data rate than the mapped signal 102. In a preferred embodiment, the mapped signal 102 is interpolated to the data rate of the decimated signal 90 in the multiplier 80.

The log mapping function is used to compress the stimulation current in a manner similar to the natural compression of the human ear. Those skilled in the art will recognize that other compressive mapping functions produce similar results, and fall within the scope of the present invention. Similarly, the embodiment described above includes a family of parallel band pass filters, but the use of a Fast Fourier Transformation (FFT) would produce similar results and is within the scope of the invention.

Thus an envelope amplitude mapping for cochlear stimulation has been presented to both reduced computational requirements, and improves performance. In applications requiring miniature devices, such reductions in computational requirements meet the important goal of extending battery life. Further, the improved performance provides more accurate hearing and thus represents a step forward in restoring natural sounding hearing to the deaf.

While the invention herein disclosed has been described by means of specific embodiments and applications thereof, numerous modifications and variations could be made thereto by those skilled in the art without departing from the scope of the invention set forth in the claims.

What is claimed is:

1. An Implantable Cochlear Stimulation (ICS) system including envelope based amplitude mapping, comprising:
   an implantable part including a cochlear electrode array; and
   a speech processor including a microphone and a signal processor, wherein the microphone converts acoustic energy into an electrical input signal provided to the signal processor, and wherein the signal processor includes:
      a bandpass filter that produces at least one filtered signal from the electrical input signal;
      an envelope detector that generates at least one envelope signal from the at least one filtered signal;
      a decimator that produces at least one decimated signal from the at least one envelope signal;
      a log mapper that produces at least one mapped signal from the at least one decimated signal; and
      a multiplier circuit that multiples the at least one mapped signal with a reference signal to produce an output signal, wherein the output signal is directed to the electrode array.

2. The system of claim 1 wherein the reference signal comprises the electrical input signal.

3. The system of claim 1 wherein the at least one decimated signal produced by the decimator is presented to an additional envelope detector, the output of which additional envelope detector is directed to an additional decimator, the output of which additional decimator is directed to the log mapper.

4. The system of claim 3 wherein the at least one decimated signal produced by the decimator comprises the reference signal that is presented to the multiplier circuit.

5. The system of claim 1 wherein the at least one envelope signal generated by the envelope detector is adapted to preserve low frequency information contained within the at least one envelope signal.

6. The system of claim 2 wherein the bandpass filter comprises a family of parallel band pass filters.

7. The system of claim 1 wherein the envelope detector comprises a full wave rectifier circuit followed by a lowpass filter.

8. The system of claim 1 including at least two envelope detectors, each providing its envelope signal to a respective decimator, and wherein each envelope detector comprises a rectifier followed by a lowpass filter.

9. The system of claim 8 wherein a first lowpass filter of a first envelope detector has a cut off frequency of between about 800 Hz to 2000 Hz.

10. The system of claim 9 wherein a second lowpass filter of a second envelope detector has a cut off frequency of between about 40 Hz to 100 Hz.

11. The system of claim 8 wherein the lowpass filter and the decimator are combined into a single Finite Impulse Response (FIR) filter.

12. An Implantable Cochlear Stimulation (ICS) system including envelope based amplitude mapping, comprising:
   an implantable part including a cochlear electrode array; and
   a speech processor including a microphone and a signal processor, wherein the microphone converts acoustic energy into an electrical input signal provided to the signal processor;
   wherein the signal processor includes:
      a network of bandpass filters that operate in parallel, each producing at least one filtered signal in a respective frequency band;
      an envelope detector associated with each bandpass filter;
      a decimator that decimates the output of the envelope detector to produce a decimated envelope;
      means for transforming the decimated envelope using a compressive function, which compressive function is the product of a log mapping of the decimated envelope and a reciprocal of the decimated envelope;
      means for scaling the filtered signal in each frequency band to obtain a stimulation current level for the implanted cochlear electrode array.

* * * * *